United States Patent
Lee et al.

(10) Patent No.: US 9,539,308 B2
(45) Date of Patent: Jan. 10, 2017

(54) COMPOSITIONS AND METHODS FOR PREVENTING ERYTHROPOIETIN-ASSOCIATED HYPERTENSION

(71) Applicants: Jong Y. Lee, Minneapolis, MN (US); John S. Lee, Northbrook, IL (US); Mary S. Lee, Northbrook, IL (US)

(72) Inventors: Jong Y. Lee, Minneapolis, MN (US); John S. Lee, Northbrook, IL (US); Mary S. Lee, Northbrook, IL (US)

( * ) Notice: Subject to any disclaimer, the term of this patent is extended or adjusted under 35 U.S.C. 154(b) by 0 days.

(21) Appl. No.: 14/042,702

(22) Filed: Sep. 30, 2013

(65) Prior Publication Data

US 2014/0120100 A1    May 1, 2014

Related U.S. Application Data

(60) Continuation of application No. 13/044,818, filed on Mar. 10, 2011, now abandoned, which is a division of
(Continued)

(51) Int. Cl.
*A61K 38/17* (2006.01)
*A61K 38/18* (2006.01)
(Continued)

(52) U.S. Cl.
CPC ......... *A61K 38/179* (2013.01); *A61K 38/1816* (2013.01); *A61K 39/3955* (2013.01);
(Continued)

(58) Field of Classification Search
None
See application file for complete search history.

(56) References Cited

U.S. PATENT DOCUMENTS 6,696,056 B1 *    2/2004    Cheung et al. .............. 424/85.1

OTHER PUBLICATIONS

Khankin et al., Soluble Erythropoietin Receptor Contributes to Erythropoietin Resistance in End-Stage Renal Disease., PLOS ONE, (2010), vol. 5, pp. e9246, 1st to 9th page.*

(Continued)

*Primary Examiner* — Alexander Kim
(74) *Attorney, Agent, or Firm* — Hakanson Patent Law PLC; Sten Hakanson

(57) ABSTRACT

The inventors have discovered that both soluble erythropoietin-binding protein and antibodies against the erythropoietin-binding protein, when they are administered to a mammal along with erythropoietin (Epo), prevent or reduce the blood pressure increase normally caused by erythropoietin, while not affecting the hematocrit increase that is the purpose of Epo treatment. The invention provides a method of treating anemia in a mammal involving: administering erythropoietin (Epo) to the mammal; and administering to the mammal an agent selected from a soluble Epo-binding protein (Epo-bp), a recognition protein that binds Epo receptor on an extracellular soluble portion of the Epo receptor, and a combination thereof. The invention also provides a method of reducing hypertension in a mammal receiving Epo, and pharmaceutical compositions containing a soluble Epo-bp and/or a recognition protein that binds Epo receptor on an extracellular soluble portion of the Epo receptor.

2 Claims, 5 Drawing Sheets

Circadian blood pressure variation in various treatments

Related U.S. Application Data application No. 10/848,689, filed on May 17, 2004, now abandoned.

(51) Int. Cl.
    *A61K 39/395*      (2006.01)
    *C07K 16/28*      (2006.01)
    *A61K 39/00*      (2006.01)

(52) U.S. Cl.
    CPC .... *C07K 16/2863* (2013.01); *A61K 2039/505* (2013.01); *C07K 2317/55* (2013.01)

(56) References Cited

OTHER PUBLICATIONS

Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
P02768 human serum albumin (last viewed on Jun. 26, 2015).*
P14753 (EPOR_Mouse), last viewed on Jun. 26, 2015.*
Erythropoietin (last viewed on Aug. 2, 2012).*
Branden and Tooze, Introduction to Protein Structure (1999), 2nd edition, Garland Science Publisher, pp. 3-12.*
DIAPEDIA (last viewed on May 11, 2016).*

* cited by examiner

Figure 1. Circadian blood pressure variation in various treatments

Figure 2. Circadian blood pressure variation in various treatments

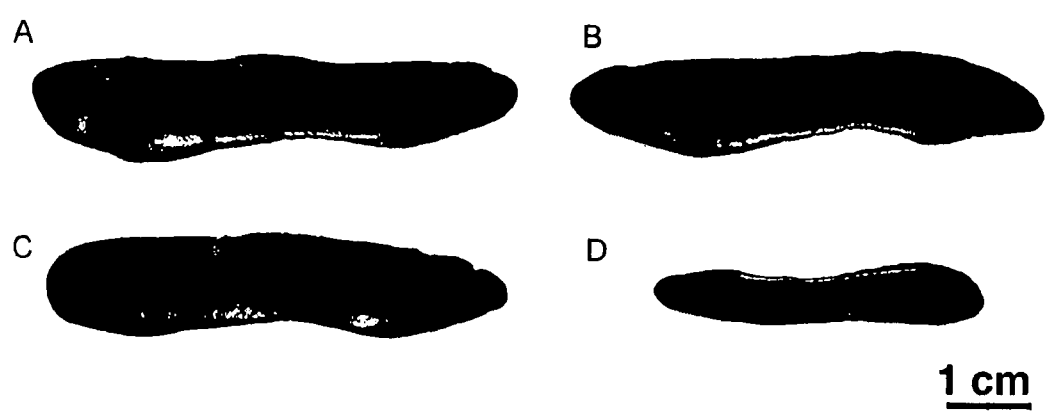
Figure 4. Splenomegaly characterized in erythropoietin treated rats.

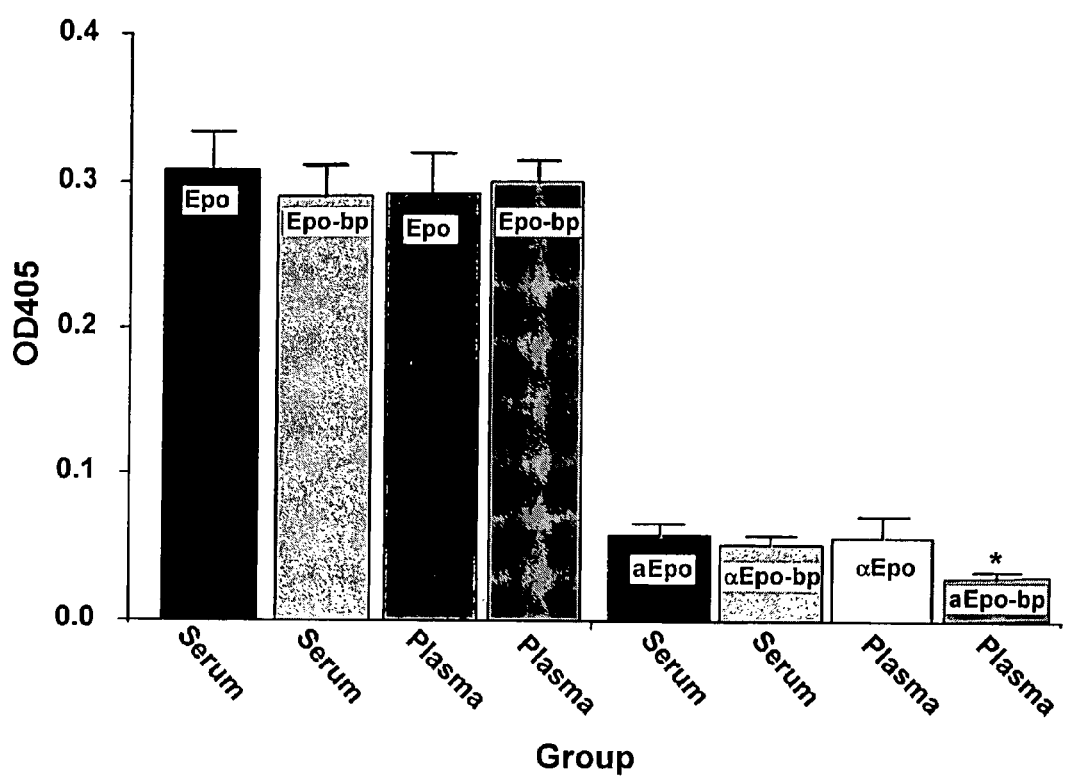
Figure 5. Optical density of Epo, Epo-bp and their antibodies in serum or plasma samples.

SEQUENCE LISTING

```
<160> NUMBER OF SEQ ID NOS: 8

<210> SEQ ID NO 1
<211> LENGTH: 508
<212> TYPE: PRT
<213> ORGANISM: Homo Sapiens
<220> FEATURE:
<221> NAME/KEY: SEQID1
<222> LOCATION: (1)..(508)
<300> PUBLICATION INFORMATION:
<301> AUTHORS: Winkelmann, J,C. et al.
<302> TITLE: The Gene for the Human Erythropoietin Receptor: Analysis of
      the Coding Sequence and Assignment to Chromosome 19p
<303> JOURNAL: Blood
<304> VOLUME: 76
<305> ISSUE: 1
<306> PAGES: 24-30
<307> DATE: 1990-07-01
<313> RELEVANT RESIDUES IN SEQ ID NO: (1)..(508)

<400> SEQUENCE: 1

Met Asp His Leu Gly Ala Ser Leu Trp Pro Gln Val Gly Ser Leu Cys
1               5                   10                  15
```

-continued

Leu Leu Leu Ala Gly Ala Ala Trp Ala Pro Pro Asn Leu Pro Asp
             20                  25              30

Pro Lys Phe Glu Ser Lys Ala Ala Leu Leu Ala Arg Gly Pro Glu
         35                  40                  45

Glu Leu Leu Cys Phe Thr Glu Arg Leu Glu Asp Leu Val Cys Phe Trp
             50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                 85                  90                  95

Pro Thr Ala Arg Gly Arg Val Arg Phe Trp Cys Ser Leu Pro Thr Ala
                100                 105                 110

Asp Thr Ser Ser Phe Val Pro Leu Glu Leu Arg Val Thr Ala Ala Ser
            115                 120                 125

Gly Ala Pro Arg Tyr His Arg Val Ile His Ile Asn Glu Val Val Leu
        130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Arg Pro Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
210                 215                 220

Ala Glu Pro Ser Phe Gly Gly Phe Trp Ser Ala Trp Ser Glu Pro Val
225                 230                 235                 240

Ser Leu Leu Glu Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
        340                 345                 350

Gly Pro Leu Leu Glu Pro Val Gly Ser Glu His Ala Gln Asp Thr Tyr
    355                 360                 365

Leu Val Leu Asp Lys Trp Leu Leu Pro Arg Asn Pro Pro Ser Glu Asp
370                 375                 380

Leu Pro Gly Pro Gly Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
                405                 410                 415

Glu Gly Ala Ser Ala Ala Ser Phe Glu Tyr Thr Ile Leu Asp Pro Ser
        420                 425                 430

Ser Gln Leu Leu Arg Pro Trp Thr Leu Cys Pro Glu Leu Pro Pro Thr

```
                     435                 440                 445
Pro Pro His Leu Lys Tyr Leu Tyr Leu Val Val Ser Asp Ser Gly Ile
    450                 455                 460

Ser Thr Asp Tyr Ser Ser Gly Asp Ser Gln Gly Ala Gln Gly Gly Leu
465                 470                 475                 480

Ser Asp Gly Pro Tyr Ser Asn Pro Tyr Glu Asn Ser Leu Ile Pro Ala
                485                 490                 495

Ala Glu Pro Leu Pro Pro Ser Tyr Val Ala Cys Ser
            500                 505

<210> SEQ ID NO 2
<211> LENGTH: 226
<212> TYPE: PRT
<213> ORGANISM: Homo Sapiens
<220> FEATURE:
<221> NAME/KEY: SEQID2
<222> LOCATION: (1)..(226)
<300> PUBLICATION INFORMATION:
<301> AUTHORS: Winkelmann, J.C.
<302> TITLE: The Gene for the Human Erythropoietin Receptor: Analysis of
      the Coding Sequence and /assignment to Chromosome 19p
<303> JOURNAL: Blood
<304> VOLUME: 76
<305> ISSUE: 1
<306> PAGES: 24-30
<307> DATE: 1992-07-01
<313> RELEVANT RESIDUES IN SEQ ID NO: (26)..(250)

<400> SEQUENCE: 2

Ala Pro Pro Pro Asn Leu Pro Asp Pro Lys Phe Glu Ser Lys Ala Ala
1               5                   10                  15

Leu Leu Ala Ala Arg Gly Pro Glu Glu Leu Leu Cys Phe Thr Glu Arg
                20                  25                  30

Leu Glu Asp Leu Val Cys Phe Trp Glu Glu Ala Ala Ser Ala Gly Val
            35                  40                  45

Gly Pro Gly Asn Tyr Ser Phe Ser Tyr Gln Leu Glu Asp Glu Pro Trp
        50                  55                  60

Lys Leu Cys Arg Leu His Gln Ala Pro Thr Ala Arg Gly Arg Val Arg
65                  70                  75                  80

Phe Trp Cys Ser Leu Pro Thr Ala Asp Thr Ser Ser Phe Val Pro Leu
                85                  90                  95

Glu Leu Arg Val Thr Ala Ala Ser Gly Ala Pro Arg Tyr His Arg Val
            100                 105                 110

Ile His Ile Asn Glu Val Val Leu Leu Asp Ala Pro Val Gly Leu Val
        115                 120                 125

Ala Arg Leu Ala Asp Glu Ser Gly His Val Val Leu Arg Trp Leu Pro
130                 135                 140

Pro Pro Glu Thr Pro Met Thr Ser His Ile Arg Tyr Glu Val Asp Val
145                 150                 155                 160

Ser Ala Gly Asn Arg Pro Gly Ser Val Gln Arg Val Glu Ile Leu Glu
                165                 170                 175

Gly Arg Thr Glu Cys Val Leu Ser Asn Leu Arg Gly Arg Thr Arg Tyr
            180                 185                 190

Thr Phe Ala Val Arg Ala Arg Met Ala Glu Pro Ser Phe Gly Gly Phe
        195                 200                 205

Trp Ser Ala Trp Ser Glu Pro Val Ser Leu Leu Glu Pro Ser Asp Leu
    210                 215                 220

Asp Pro
225
```

<210> SEQ ID NO 3
<211> LENGTH: 193
<212> TYPE: PRT
<213> ORGANISM: Homo Sapiens
<220> FEATURE:
<221> NAME/KEY: SEQID3
<222> LOCATION: (1)..(193)
<300> PUBLICATION INFORMATION:
<308> DATABASE ACCESSION NUMBER: NP_000790
<309> DATABASE ENTRY DATE: 2003-12-23
<313> RELEVANT RESIDUES IN SEQ ID NO: (1)..(193)

<400> SEQUENCE: 3

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Glu
                20                  25                  30

Ile Cys Asn Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Leu Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Gln Leu Gly
            115                 120                 125

Leu Arg Ser Leu Thr Thr Leu Leu Arg Ala Leu Arg Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg
```

<210> SEQ ID NO 4
<211> LENGTH: 1849
<212> TYPE: DNA
<213> ORGANISM: Homo Sapiens
<300> PUBLICATION INFORMATION:
<308> DATABASE ACCESSION NUMBER: NM_000121
<309> DATABASE ENTRY DATE: 2003-12-20
<313> RELEVANT RESIDUES IN SEQ ID NO: (1)..(1849)

<400> SEQUENCE: 4

```
acttagaggc gcctggtcgg gaagggcctg gtcagctgcg tccggcggag gcagctgctg      60
acccagctgt ggactgtgcc gggggcgggg gacggagggg caggagccct gggctccccg     120 tgcgggggc tgtatcatgg accacctcgg ggcgtccctc tggccccagg tcggctccct     180
ttgtctcctg ctcgctgggg ccgcctgggc gccccgcct aacctcccgg accccaagtt     240
cgagagcaaa gcggccttgc tggcggcccg ggggcccgaa gagcttctgt gcttcaccga     300
gcggttggag gacttggtgt gtttctggga ggaagcggcg agcgctgggg tgggcccggg     360
caactacagc ttctcctacc agctcgagga tgagccatgg aagctgtgtc gcctgcacca     420
```

-continued

```
ggctcccacg gctcgtggtg cggtgcgctt ctggtgttcg ctgcctacag ccgacacgtc      480
gagcttcgtg cccctagagt tgcgcgtcac agcagcctcc ggcgctccgc gatatcaccg      540
tgtcatccac atcaatgaag tagtgctcct agacgccccc gtggggctgg tggcgcggtt     600
ggctgacgag agcggccacg tagtgttgcg ctggctcccg ccgcctgaga cacccatgac     660
gtctcacatc cgctacgagg tggacgtctc ggccggcaac ggcgcaggga cgtacagag     720 ggtggagatc ctggagggcc gcaccgagtg tgtgctgagc aacctgcggg gccggacgcg     780
ctacaccttc gccgtccgcg cgcgtatggc tgagccgagc ttcggcggct tctggagcgc     840
ctggtcggag cctgtgtcgc tgctgacgcc tagcgacctg accccctca tcctgacgct     900 ctccctcatc ctcgtggtca tcctggtgct gctgaccgtg ctcgcgctgc tctcccaccg     960
ccgggctctg aagcagaaga tctggcctgg catcccgagc ccagagagcg agtttgaagg    1020
cctcttcacc acccacaagg gtaacttcca gctgtggctg taccagaatg atggctgcct    1080
gtggtggagc ccctgcaccc ccttcacgga ggacccacct gcttccctgg aagtcctctc    1140
agagcgctgc tgggggacga tgcaggcagt ggagccgggg acagatgatg agggcccccct    1200 gctggagcca gtgggcagtg agcatgccca ggatacctat ctggtgctgg acaaatggtt    1260
gctgccccgg aacccgccca gtgaggacct cccagggcct ggtggcagtg tggacatagt    1320
ggccatggat gaaggctcag aagcatcctc ctgctcatct gctttggcct cgaagcccag    1380
cccagaggga gcctctgctg ccagctttga gtacactatc ctggacccca gctcccagct    1440
cttgcgtcca tggacactgt gccctgagct gccccctacc ccaccccacc taaagtacct    1500
gtaccttgtg gtatctgact ctggcatctc aactgactac agctcagggg actcccaggg    1560
agcccaaggg ggcttatccg atggccccta ctccaaccct tatgagaaca gccttatccc    1620
agccgctgag cctctgcccc ccagctatgt ggcttgctct taggacacca ggctgcagat    1680
gatcagggat ccaatatgac tcagagaacc agtgcagact caagacttat ggaacaggga    1740
tggcgaggcc tctctcagga gcaggggcat tgctgatttt gtctgcccaa tccatcctgc    1800
tcaggaaacc acaaccttgc agtatttttta aatatgtata gttttttttg              1849
```

<210> SEQ ID NO 5
<211> LENGTH: 23
<212> TYPE: DNA
<213> ORGANISM: E. Coli

<400> SEQUENCE: 5

```
ttggatccgc gccccgcct aac                                                23
```

<210> SEQ ID NO 6
<211> LENGTH: 22
<212> TYPE: DNA
<213> ORGANISM: E. Coli

<400> SEQUENCE: 6

```
tgaattcggg gtccaggtcg ct                                                22
```

<210> SEQ ID NO 7
<211> LENGTH: 6
<212> TYPE: PRT
<213> ORGANISM: E. Coli

<400> SEQUENCE: 7

Leu Val Pro Arg Gly Ser
1               5

```
<210> SEQ ID NO 8
<211> LENGTH: 228
<212> TYPE: PRT
<213> ORGANISM: E. Coli

<400> SEQUENCE: 8

Gly Ser Ala Pro Pro Asn Leu Pro Asp Pro Lys Phe Glu Ser Lys
1               5                   10                  15

Ala Ala Leu Leu Ala Ala Arg Gly Pro Glu Glu Leu Leu Cys Phe Thr
                20                  25                  30

Glu Arg Leu Glu Asp Leu Val Cys Phe Trp Glu Glu Ala Ala Ser Ala
            35                  40                  45

Gly Val Gly Pro Gly His Tyr Ser Phe Ser Tyr Gln Leu Glu Asp Glu
        50                  55                  60

Pro Thr Lys Leu Cys Arg Leu His Gln Ala Pro Thr Ala Arg Gly Ala
65                  70                  75                  80

Val Arg Phe Trp Cys Ser Leu Pro Thr Ala Asp Thr Ser Ser Phe Val
                85                  90                  95

Pro Leu Glu Leu Arg Val Thr Ala Ala Ser Gly Ala Pro Arg Tyr His
                100                 105                 110

Arg Val Ile His Ile Asn Glu Val Val Leu Leu Asp Ala Pro Val Gly
            115                 120                 125

Leu Val Ala Arg Leu Ala Asp Glu Ser Gly His Val Val Leu Arg Trp
        130                 135                 140

Leu Pro Pro Pro Glu Thr Pro Met Thr Ser His Ile Arg Tyr Glu Val
145                 150                 155                 160

Asp Val Ser Ala Gly Asn Gly Ala Gly Ser Val Gln Arg Val Glu Ile
                165                 170                 175

Leu Glu Gly Arg Thr Glu Cys Val Leu Ser Asn Leu Arg Gly Arg Thr
            180                 185                 190

Arg Tyr Thr Phe Ala Val Arg Ala Arg Met Ala Glu Pro Ser Phe Gly
        195                 200                 205

Gly Phe Trp Ser Ala Trp Ser Glu Pro Val Ser Leu Leu Thr Pro Ser
    210                 215                 220

Asp Leu Asp Pro
225
```

COMPOSITIONS AND METHODS FOR PREVENTING ERYTHROPOIETIN-ASSOCIATED HYPERTENSION

This nonprovisional patent application claims priority from and is a copending continuation of U.S. application Ser. No. 13/044,818 filed Mar. 10, 2011, which was a copending continuation of U.S. application Ser. No. 10/848,689, filed May 17, 2004, which applications are incorporated herein by reference thereto.

The research and development of the invention described herein did not involve any federally sponsored funding.

BACKGROUND OF THE INVENTION

Erythropoietin is sold under the labels PROCRIT (epoetin), EPOGEN (epoetin), and ARANESP (darbepoetin). Erythropoietin is indicated for treatment of anemia, particularly anemia associated with chronic renal failure and cancer chemotherapy. Erythropoietin (Epo), an angiogenic factor, increases hematocrit and hemoglobin concentrations via the stimulation of erythropoiesis, resulting in increased blood viscosity (1-5) and blood pressure (1-14). In clinical studies, approximately one-third of hemodialysis patients treated with recombinant human Epo have shown an increase in blood pressure. Epo has been postulated to increase peripheral vascular resistance and decrease cardiac output due to increased viscosity (6). Others have suggested additional mechanisms for Epo-caused hypertension, such as hypervolemia, increased plasma renin and angiotensin, along with adrenergic over activity, increased plasma arginine vasopressin, decreased kinins and prostaglandins (15). An excessive, lasting elevation of circadian amplitude, blood pressure over-swinging and an elevation of blood pressure may be based on vasomotor chronome (time structure) alteration. Hormones and other agents, in part on a genetic basis, may be contributing factors to the circadian blood pressure variation. Hypertension is one of the most important risk factors in the development of cardiovascular complications. Hypertension is affected significantly by circadian rhythms. Hormonal concentration in the body fluctuates during the day and night with prominent spontaneous circadian (about-24-hour) changes that affect blood pressure and heart rate. There are also sufficiently important rhythms that can make the difference between the stimulation versus the inhibition of a malignancy. Epo is a 34 kDa glycoprotein hormone that is produced by the interstitial cells in the peritubular capillary bed of the mammalian kidney and the perivenenous hepatocytes of the liver (3). Epo is secreted in response to hypoxia to coordinate erythropoiesis as a primary inducer and regulator of red-cell differentiation by suppressing apoptosis and triggering cell division and terminal maturation of blood cell progenitors (16). These effects are mediated through the binding of Epo to specific cell surface receptors (17). The primary structure of human Epo has been known since the mid-1980s (18,19), but the structural features of the Epo molecule that confer its biological activity are largely unknown. Human Epo contains two disulfide bonds that link cysteine 29 with cysteine 33, and cysteine 7 with cysteine 161. Both bonds are essential for biological activity (18). Epoetin (recombinant human erythropoietin) was produced following isolation of the human gene and its expression in a Chinese hamster's ovarian cell line (4).

The recombinant Epo is a 165-amino acid mature protein that differs from the mature native protein only in lacking the carboxyl terminus arginine of the native protein. Native human Epo is translated as a 193-amino acid peptide, from which a 27-amino-acid leader sequence is cleaved off (19, 20). Recombinant Epo has an apparent molecular weight of about 30.4 kDa, appears to be immunologically equivalent to the endogenous hormone, and exhibits full biological activity (19).

Epo-treated humans and animals exhibit increased hematocrit % and increased hemoglobin via the stimulation of erythropoiesis (2-5). Some study results suggest that increased hematocrit levels are correlated with an increased blood pressure in humans (20). Other studies involving the treatment of anemia with Epo showed increased hematocrit concentrations and resulting elevated blood severe enough to require treatment with antihypertensive medication pressure in 20-30% of patients (5). Hypertension is the most frequent and most important complication from treatment with erythropoietin. Furthermore, although the goal of Epo treatment is to increase hematocrit and hemoglobin, it has been found that the greater the increase of hematocrit, the greater the risk of mortality and cardiovascular events, see for example the "Procrit" website at "Procrit dot com" on the world wide web (PROCRIT warnings,). This may be due to blood pressure rise, since the extent of blood pressure rise has been shown to correlate with the extent of hematocrit increase (20). The epoetin label warns that patients with uncontrolled hypertension should not be treated with epoetin.

SUMMARY OF THE INVENTION

The inventors have discovered that a soluble Epo-binding protein, which is a soluble fragment of the membrane protein Epo receptor, when administered to mammals along with Epo, prevents the blood pressure increase ordinarily caused by Epo, while not affecting the rise in hemoglobin and hematocrit that is the goal of Epo treatment. An antibody against Epo-binding protein was also found to prevent the Epo-caused blood pressure increase while not affecting the Epo-induced hematocrit rise. Accordingly, the invention provides a method of treating anemia in a mammal involving: administering erythropoietin (Epo) to the mammal; and administering to the mammal an agent selected from a soluble Epo-binding protein (Epo-bp), a recognition protein that binds Epo receptor on an extracellular soluble portion of the Epo receptor, and a combination thereof. Another embodiment of the invention provides a method of reducing hypertension in a mammal receiving Epo involving administering to the mammal an agent selected from a soluble Epo-binding protein (Epo-bp), a recognition protein that binds Epo receptor on an extracellular soluble portion of the Epo receptor, and a combination thereof. Another embodiment of the invention provides use of a recognition protein that binds Epo receptor on an extracellular soluble portion of the Epo receptor in medical therapy. Another embodiment of the invention provides use of a recognition protein that binds Epo receptor on an extracellular soluble portion of the Epo receptor to prepare a medicament effective to reduce erythropoietin-induced hypertension. Another embodiment of the invention provides use of a soluble erythropoietin-binding protein in medical therapy.

Another embodiment of the invention provides use of a soluble erythropoietin-binding protein to prepare a medicament effective to reduce erythropoietin-induced hypertension. Another embodiment of the invention provides a pharmaceutical composition including: erythropoietin; and an agent selected from a soluble Epo-binding protein (Epo-bp), a recognition protein that binds Epo receptor on an extracellular soluble portion of the Epo receptor, and a combination thereof. Another embodiment of the invention provides a pharmaceutical composition including: a recognition protein that binds Epo receptor on an extracellular soluble portion of the Epo receptor. Another embodiment of the invention provides a pharmaceutical composition including: a soluble Epo-binding protein.

BRIEF DESCRIPTION OF THE DRAWINGS

FIG. 4 is the outline of photographs of spleens isolated from rats treated with Epo (panels A, B, and C), or saline (panel D).

FIG. 5 is a bar graph of optical density from immunodetection of Epo, VEpo, Epo-bp, and VEpo-bp in serum and plasma of human volunteers. Error bars represent standard error, SEM.

DETAILED DESCRIPTION

Definitions

Figure 1:
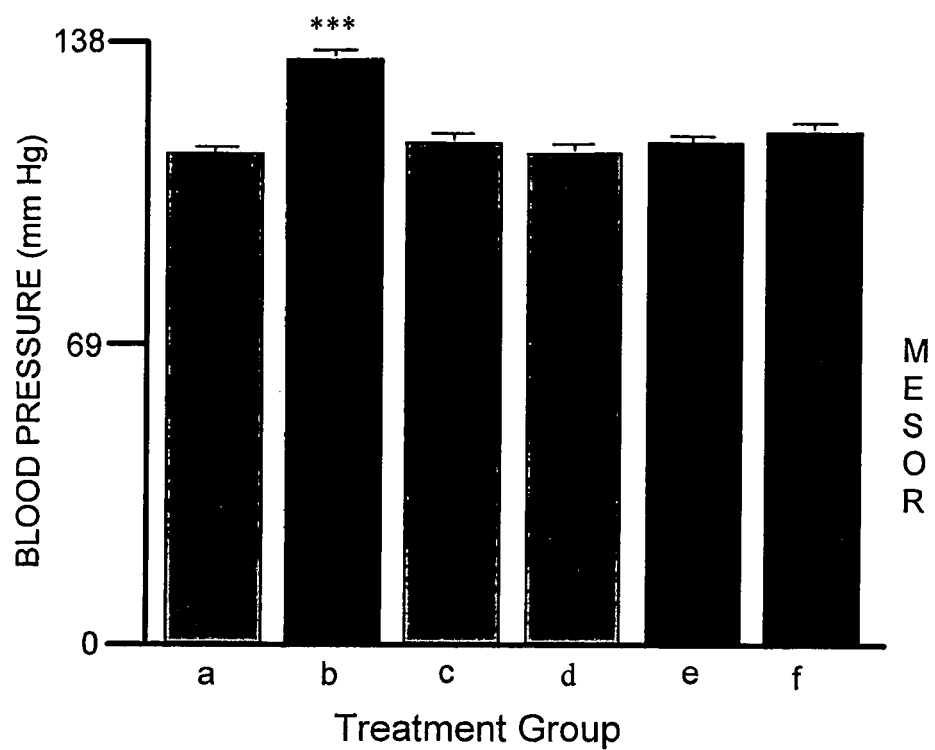
FIG. 1 is a bar graph showing the average circadian blood pressure of each of the treatment groups of rats treated with Epo and other agents. Error bars represent standard error, SEM.

"Erythropoietin" as used herein includes erythropoietin isolated from natural sources and recombinant or engineered erythropoietin that has the biological activity of erythropoietin of stimulating red blood cell production. It includes epoetin and darbepoetin. Preferably, the erythropoietin has at least 70%, more preferably at least 90%, amino acid sequence identity with human erythropoietin, SEQ ID NO:3. Sequence identity is calculated using the default BLAST parameters for nucleotide sequence comparison at the PubMed website seen on the world wide web as contained within the website of the "National Center for Biotechnology Information (NCIB)" at ncib dot nlm dot nih dot gov/pubmed/.

As used herein, "a soluble Epo-binding protein" refers to a protein that is not an antibody, is water-soluble, binds erythropoietin with high affinity, and when administered with Epo to mammals is effective at reducing an Epo-induced blood pressure rise in the mammals. Preferably, the KD of the protein for binding with erythropoietin is less than 10 µM, more preferably less than 1 µM, more preferably still less than 100 nM, and most preferably less than 20 nM. KD can be determined by competition binding assays such as described in Example 6 of U.S. Pat. No. 5,843,726. Preferably, the soluble Epo-binding protein is or includes sequences from or sequences homologous to the soluble portion of an Epo receptor. The human Epo receptor sequence is SEQ ID NO:1 (Winkelmann, J. C., et al., 1990, Blood 76: 24-30). The soluble portion of the human Epo receptor is residues 25-250 of SEQ ID NO:1. In a particular embodiment, the residues of the Epo-binding protein responsible for binding Epo are at least 70% identical, more preferably at least 80% identical, more preferably at least 90% identical, most preferably identical, to the corresponding residues of SEQ ID NO:1.

As used herein, "an extracellular soluble portion of an Epo receptor" refers to the portion of the Epo receptor that is exposed on the extracellular surface of the cell in the aqueous environment. Specifically, it refers to SEQ ID NO:2, which is residues 25-250 of SEQ ID NO:1 (the human Epo receptor), or to the homologous soluble residues of another Epo receptor protein.

As used herein, "a recognition protein that binds Epo receptor on an extracellular soluble portion of the Epo receptor" refers to a protein that binds the extracellular soluble portion of Epo receptor and that, when administered to mammals along with Epo, reduces an Epo-induced blood pressure rise in the mammals. The recognition protein can be a complete antibody raised against an Epo receptor or against an Epo-binding protein, where the antibody binds the soluble portion of Epo receptor, or a binding fragment of such a complete antibody. The recognition protein can also be a non-antibody protein or peptide (e.g., a protein or peptide selected by phage display binding) that binds to the extracellular soluble portion of the human Epo receptor or of another mammalian Epo receptor with a binding affinity of at least 105 liters per mole, more preferably 106, more preferably at least 107, most preferably at least 108 liters per mole.

As used herein, the term "antibody" includes complete antibodies and antigen-binding fragments of complete antibodies, e.g., Fab or F(ab')2 antibodies. The term "antibody" also includes both monoclonal and polyclonal antibodies (e.g., antiserum).

The term "reducing hypertension" by administering an agent includes preventing or reducing an increase in blood pressure that otherwise occurs in a significant fraction of a population when the agent is not administered.

Description:

The methods of the invention involve administering to the mammal an agent selected from a soluble Epo-binding protein (Epo-bp), a recognition protein that binds Epo receptor on an extracellular soluble portion of the Epo receptor, and a combination thereof. In some embodiments of the invention, the agent is a soluble Epo-bp. In some embodiments, the soluble Epo-bp contains a fragment of a soluble portion of a mammalian Epo receptor.

In particular embodiments the soluble Epo-bp comprises a fragment of at least 30 residues of SEQ ID NO:2 (residues 25-250 of human Epo receptor, SEQ ID NO: 1). SEQ ID NO:2 is the extracellular soluble portion of the human Epo receptor. In other particular embodiments, the soluble Epo-bp comprises a fragment of at least 15, at least 50, at least 100, at least 150, or at least 200 residues of SEQ ID NO:2.

In particular embodiments, the soluble Epo-bp includes or is SEQ ID NO:2. The soluble Epo-bp that is SEQ ID NO:2 can be expressed as described in U.S. Pat. No. 5,843,726. In general terms, SEQ ID NO:2 is expressed as a fusion protein with a glutathione S-transferase (GST) N-terminal leader sequence. SEQ ID NO:2 is separated from the GST leader sequence by a thrombin cleavage site. The expressed fusion protein is cleaved with thrombin to release SEQ ID NO:2.

The Epo-bp of SEQ ID NO:2 is found naturally in human serum and plasma, possibly produced as a cleavage product of Epo receptor (see Example 2 below). In particular embodiments, the soluble Epo-bp has at least 70%, at least 80%, or at least 90% amino acid sequence identity to SEQ ID NO:2, as calculated using the default BLAST parameters for nucleotide sequence comparison at the PubMed website seen on the world wide web as contained within the website of the "National Center for Biotechnology Information (NCIB)" at ncib dot nlm dot nih dot gov/pubmed/.

In some embodiments of the invention, the soluble Epo-bp is SEQ ID NO:8, which is SEQ ID NO:2 with the additional two residues Gly-Ser at the amino terminus. In one embodiment of the invention, the soluble Epo-bp is a product of a process comprising: expressing a fusion protein and cleaving it with thrombin. The fusion protein consists essentially of a first polypeptide segment having a thrombin proteolytic cleavage site at its carboxyl terminus, and a second polypeptide segment consisting essentially of SEQ ID NO:2. The amino terminus of the second segment is covalently coupled to the carboxyl terminus of the first segment. The soluble Epo-bp is produced by cleaving the fusion protein with thrombin.

In one embodiment of the invention, the soluble Epo-bp is a product of a process comprising: expressing a fusion protein comprising SEQ ID NO:2 linked at its amino terminus to a peptide sequence of Leu-Val-Pro-Arg-Gly-Ser (SEQ ID NO:7), and cleaving the fusion protein with thrombin.

In one embodiment of the invention, the soluble Epo-bp is a product of a process comprising: expressing a fusion protein consisting of: (a) a first polypeptide segment having an amino terminus and a carboxyl terminus, said segment having SEQ ID NO:7 at its carboxyl terminus; and (b) a second polypeptide segment consisting of SEQ ID NO:2, the second polypeptide segment covalently coupled to the carboxyl terminus of the first polypeptide segment; and cleaving the fusion protein with thrombin.

In other particular embodiments of the methods of the invention, the agent is a recognition protein that binds Epo receptor on an extracellular soluble portion of the Epo receptor. The recognition protein may exert its effect of reducing the Epo-induced blood pressure increase by binding to the extracellular soluble portion of intact Epo receptor molecules in membranes, or it may exert its effect by binding to the soluble Epo-binding protein that exists naturally circulating in blood (which has the same amino acid sequence as the extracellular soluble portion of the Epo receptor, and may be a proteolytic product of the receptor), or by both of these mechanisms or other unknown mechanisms. Describing this embodiment of the agent as "a recognition protein that binds Epo receptor on an extracellular soluble portion of the Epo receptor" is intended to describe a characteristic of the recognition protein, and not to necessarily describe the mechanism of action of the recognition protein.

In a particular embodiment, the recognition protein binds SEQ ID NO:2. That is, the recognition protein recognizes and binds to some sequence within SEQ ID NO:2. The recognition protein could, for instance, be an antibody raised against SEQ ID NO:2, an antibody raised against the Epo receptor where the antibody binds to SEQ ID NO:2, or an antibody raised against a peptide fragment of SEQ ID NO:2. In particular embodiments, the recognition protein is an antibody. In particular embodiments, the antibody is a complete antibody. In particular embodiments, the antibody is an antibody fragment. For instance, the antibody fragment may be an Fab, Fab', or F(ab')2, or Fv. In particular embodiments, the antibody is an antibody against SEQ ID NO:2.

In other particular embodiments, the recognition protein is a non-antibody protein or peptide. For instance, it can be a recognition peptide or protein selected by phage display. Methods for selection of binding peptides using phage display are disclosed in Sidhu S S, Lowman H B, Cunningham B C, and Wells J A: Phage display for selection of novel binding peptides. *Methods in Enzymology* 2000; 328:333-363.

In a particular embodiment, the agent is a combination of a soluble Epobinding protein and a recognition protein that binds Epo receptor on an extracellular soluble portion of the receptor.

Epo and the agent may be administered separately or together.

In particular embodiments, the amount of the agent administered is at least equimolar with the amount of Epo administered. In particular embodiments, the amount of the agent administered is about equimolar with the amount of Epo administered. For instance, the moles of the agent administered may be between 75% and 125% of the mole of Epo administered. In particular embodiments of the method of treating anemia, the agent reduces an erythropoietin-induced blood pressure rise in the mammal. That is, the blood pressure of the mammal rises less when the mammal receives Epo and the agent, than when the mammal receives Epo alone. Preferably, when Epo is administered to a mammal with an equimolar amount of the agent, blood pressure increases no more than 75% as much as it rises when Epo is administered alone to the mammal, more preferably no more than 50% as much as it increases when Epo is administered alone to the mammal. One embodiment of the invention is a pharmaceutical composition containing a recognition protein that binds Epo receptor on an extracellular soluble portion of the Epo receptor. Another pharmaceutical composition of the invention includes erythropoietin and an agent selected from a soluble Epo-binding protein, a recognition protein that binds Epo receptor on an extracellular soluble portion of the Epo receptor, and a combination thereof.

Another pharmaceutical composition of the invention includes a soluble Epo-binding protein. Typically, the pharmaceutical compositions include a pharmaceutically acceptable diluent or carrier. In one embodiment of the pharmaceutical compositions containing the recognition protein, the recognition protein is an antibody against SEQ ID NO:2. In one embodiment of the pharmaceutical compositions containing the soluble Epo-binding protein, the Epo-binding protein is SEQ ID NO:2.

Other particular embodiments of the agent, the soluble Epo-binding protein, and the recognition protein that binds Epo receptor on an extracellular soluble portion of the Epo receptor are as described for the methods of the invention.

Raising Antibodies:

To generate antibodies, Epo receptor or Epo-bp can be administered directly to a mammal, or the proteins or peptide fragments thereof can be coupled to a carrier protein. Suitable carrier proteins include keyhole limpet hemocyanin, bovine serum albumin, and ovalbumin. Methods of coupling to the carrier protein include single step glutaraldehyde coupling and other methods disclosed in Harlow, Ed et al., *Antibodies: a laboratory manual*, Cold Spring Harbor Laboratory (1988). The immunogen is used to immunize a vertebrate animal in order to induce the vertebrate to generate antibodies. Preferably the immunogen is injected along with an adjuvant such as Freund's adjuvant, to enhance the immune response. Suitable vertebrates include rabbits, mice, rats, hamsters, goats, sheep, and chickens.

Hybridomas to synthesize monoclonal antibodies can be prepared by methods known in the art. See, for instance, Wang, H., et al., *Antibody Expression and Engineering*, Am. Chem. Soc., Washington, D.C. (1995). Polyclonal and monoclonal antibodies can be isolated by methods known in the art. See, for instance, id. and Harlow et al.

Native antibodies are tetramers of two identical light (L) chains and two identical heavy (H) chains. The L and H chains each have variable domains that are responsible for antigen recognition and binding. The variability in the variable domains is concentrated in the complementarity determining regions (CDRs). An antibody that is contemplated for use in the present invention can be in any of a variety of forms, including a whole immunoglobulin, an antibody fragment such as Fv, Fab, and similar fragments, a single chain antibody that includes the CDR, and like forms, all of which fall under the broad term "antibody" as used herein.

The term "antibody fragment" refers to an antigen-binding portion of a full-length antibody. Antibody fragments can be as small as about 4 amino acids, about 10 amino acids, or about 30 amino acids or more. Some types of antibody fragments are the following:

1. Fab is the fragment that contains a monovalent antigen-binding fragment of an antibody molecule. A Fab fragment can be produced by digestion of whole antibody with the enzyme papain to yield an intact light chain and a portion of one heavy chain. Two Fab fragments are obtained per whole antibody molecule.

2. Fab' is the fragment of an antibody that can be obtained by treating whole antibody with pepsin, followed by reduction to yield an intact light chain and a portion of the heavy chain. Two Fab' fragments are obtained per whole antibody molecule. Fab' fragments differ from Fab fragments by the addition of a few residues at the carboxyl terminus of the heavy chain CH1 domain including one or more cysteines.

3. F(ab')2 is the fragment that can be obtained by digestion of whole antibody with pepsin, without reduction. F(ab')2 is a dimer of two Fab' fragments held together by two disulfide bonds.

4. Fv is the minimum antibody fragment that contains a complete antigen recognition and binding site. Fv consists of a dimer of one H and one L chain variable domain in a tight, non-covalent association (VH-VL dimer). It is in this configuration that the three CDRs of each variable domain interact to define an antigen-binding site. Collectively, the six CDRs confer antigen binding specificity to the antibody. However, even a single variable domain (or half of an Fv comprising only three CDRs specific for an antigen) has the ability to bind antigen, although at a lower affinity than the complete binding site.

5. A single chain antibody (SCA) is defined as a genetically engineered molecule containing the variable region of the light chain and the variable region of the heavy chain linked by a suitable polypeptide linker as a genetically fused single chain molecule. The preparation of polyclonal antibodies is well known to those skilled in the art. See, for example, Coligan et al., in *Current Protocols in Immunology*, section 2.4.1 (1992). The preparation of monoclonal antibodies is likewise conventional. See, for example, Harlow et al., page 726.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, *Nature* 256:495 (1975), or may be made by recombinant methods, e.g., as described in U.S. Pat. No. 4,816,567. The monoclonal antibodies for use with the present invention may also be isolated from phage antibody libraries using the techniques described in Clarkson et al., *Nature* 352:624 (1991), as well as in Marks et al., *J. Mot Biol.* 222:581 (1991). Another method involves humanizing a monoclonal antibody by recombinant means to generate antibodies containing human specific and recognizable sequences. See, for review, Holmes et al., *J Immunol.* 158:2192 (1997) and Vaswani et al., *Annals Allergy, Asthma & Immunol.* 81:105 (1998).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) are identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l. Acad. Sci.* 81:6851 (1984)).

Methods of making antibody fragments are also known in the art (see, for example, Harlow and Lane, *Antibodies: a Laboratory Manual*, Cold Spring Harbor Laboratory, New York (1988)). Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using pepsin produces two monovalent Fab fragments and an Pc fragment directly. These methods are described, for example, in U.S. Pat. Nos. 4,036,945, and 4,331,647, and references contained therein. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of VH and VL chains. This association may be noncovalent or the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker bridging the two V domains. Methods for producing sFvs are described, for example, by Whitlow et al., *Methods: a Companion to Methods in Enzymology*, 2:97 (1991); Bird et al, *Science* 242:423 (1988); Ladner et al., U.S. Pat. No. 4,946,778; and Pack et al., *Bio/Technology* 11:1271(1993).

Another form of an antibody fragment is a peptide containing a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick et al., *Methods: a Companion to Methods in Enzymology*, 2:106 (1991).

The invention contemplates human and humanized forms of non-human (e.g., murine) antibodies. Such humanized antibodies are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat, goat, sheep, or rabbit having the desired specificity, affinity, and capacity.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., *Nature* 321:522 (1986); Reichmann et al., *Nature* 332:323 (1988); Presta, *Curr. Opinion Struct. Biol.* 2:593 (1992); Holmes et al., *I Immunol.* 158:2192 (1997); and Vaswani et al., *Annals Allergy, Asthma & Immunot* 81:105 (1998).

Antibodies of the invention can also be mutated to optimize their affinity, selectivity, binding strength or other desirable property. One method of mutating antibodies involves affinity maturation using phage display. Affinity maturation using phage display refers to a process described in Lowman et al., *Biochemistry* 30:10832 (1991); see also Hawkins et al., *I MoL Biol.* 254:889 (1992).

The invention will now be illustrated by the following non-limiting examples.

Example 1

The Example describes the preparation of an Epo-bp thought to have SEQ ID NO:2, as is also described in U.S. Pat. No. 5,843,726, Construction of EpoR recombinant vector. A recombinant plasmid expression vector, pJYL26, was constructed from a PCR product having the human Epo receptor extracellular soluble domain coding sequence and from the plasmid vector pGEX-2T, which was purchased from Pharmacia. PCR amplification was carried out using a frill-length human EpoR cDNA, SEQ ID NO:4, as a template. The 5'-sense primer was 5'-TTGGATCCGCGC-CCCCGCCTAAC-3' (SEQ ID NO:5). This primer has a BamH1 linker sequence at the 5' end followed by the coding sequence for amino acids 25-29 of the full-length human EpoR protein. The 3'-antisense primer was 5'-TGAAT-TCGGGGTCCAGGTCGCT-3' (SEQ ID NO:6). This primer has an EcoR1 linker followed by sequence complementary to the coding sequence for amino acids 250 through 246 of full-length EpoR. PCR was carried out as described in U.S. Pat. No. 5,843,726.

The PCR product and pGEX-2T were digested with EcoR1 and BamH1, the digested DNAs were purified with gel electrophoresis. The ligation was done with a mixture containing 1:g/:1 each of the PCR product and pGEX-2T. The ligated product was verified to be -5.5 kb. The ligated plasmid mixture was used to transform *E. coli* JM109. Colonies were grown. DNA was extracted from each transformed colony, and analyzed. Plasmid from one colony was selected after examining both EcoR1 and EcoR1 plus BamH1 digested DNA sizes in 1% agarose gels to confirm the predicted sizes. The procedures were carried out as described in U.S. Pat. No. 5,843,726, Purification of EpoRex-th fusion protein. Transformed *E. coli* containing the recombinant vector pJYL26 was grown and induced with IPTG. Cell extract was passed through a GSH-agarose column. The bound EpoRex-th was eluted with reduced glutathione. This was performed as described in U.S. Pat. No. 5,843,726. Purification of Epo-bp. EpoRex-th contains a thrombin-specific proteolytic cleavage recognition sequence separating Epo-bp from glutathione-S-transferase. The amino acid sequence of the cleavage recognition sequence is Leu-Val-Pro-ArgGly-Ser (SEQ ID NO:7). The fusion protein was cleaved with thrombin, and Epo-bp was purified by affinity binding to an Epo-agarose column. This was performed as described in U.S. Pat. No. 5,843,726. The amino terminus of the Epo-bp produced by this procedure, and thus the thrombin cleavage site, was not experimentally determined. The thrombin cleavage is believed to produce Epo-bp of SEQ ID NO:2. But, thrombin may cleave at other sites, such as between the Arg and the Gly of the recognition sequence to produce a protein having the Gly-Ser peptide attached to the amino terminus of SEQ ID NO:2 (SEQ ID NO:8).

Example 2

This Example describes experiments testing the effect of administering Epobp, which is a soluble Epo-binding protein having the amino acid sequence of SEQ ID NO:2, and an Fab antibody against Epo-bp, either with or without Epo, to rats.

Experimental Procedures:
Materials:
Glutathione (GSH)-agarose, pGEX-2T expression vector and SEPHADEX G-50 were purchased from Pharmacia (Mechanicsburg, Pa.). PCR reagents were from Perkin-Elmer Cetus (Norwalk, Conn.) and AFFIGEL® was from BioRad (Richmond, Calif.). Bacteriophage T4 DNA ligase, restriction enzymes and isopropylthio-13-Dgalactoside (IPTG) were purchased from BRL Gibco (Gaithersburg, Md.). GENECLEAN II was from Bio 101, La Jolla, Calif. Nitrocellulose was from Schleicher & Schuell Co. (Keene, N.H.). Chemiluminescence (ECL) reagents and 125I-Epo were from Amersham (Arlington Heights, Ill.) and unlabeled Epo was a gift of Chugai-Upjohn (Rosemont, Ill.). Thrombin, trypsin, phenylmethylsulfonylfluoride (PMSF), diisopropylfluorophosphate (DFP), TRITON X-100, 2,7-Dichlorofluoresein, biotin-amidocaproyl hydroazide, alkaline phosphatase conjugate, disodium pnitrophenyl phosphate, and o-phenylenediaminedihydrochloride (oPD) were from Sigma (St. Louis, Mo.). Biotinylated rabbit anti-sheep antibodies, Avidin-horse radish peroxidase, and IgG purification Kit were from Pierce Co. (Rockford, Ill.). Streptavidin peroxidase was purchased from Boehringer Manheim Corp (Indianapolis, Ind.), and microplates were from Corning Costa (Cambridge, Mass.). All 5 other chemicals were of reagent grade.

Epo-bp, Fab antibody against Epo-bp (aEpo-bp), and Fab antibody against Epo (aEpo) were prepared in our laboratory. Epo-bp was prepared as described in U.S. Pat. No. 5,843,726. Epo-bp had the amino acid sequence of SEQ ID NO:2. A full-length human EpoR cDNA (SEQ ID NO:4) was from Dr. Bernard G. Forget, Yale University. Oligonucleotides were synthesized by the microchemical facility of the Institute of Human Genetics, University of Minnesota, Minn. All other chemicals were of reagent grade.

Animal Study:

15 Male Sprague-Dawley (SD) rats were housed at the University Animal Care facility with Purina Chow and drinking water freely accessible. We examined any circadian stage-dependence of Epo effects on the blood pressure, hematocrit, body weight and spleen weight of the rats kept in an alternating light-darkness cycle from 04:00 to 18:00 for light. To seek an effective treatment time, 5-week-old rats were assigned to control or treatment groups, each group consisting of 6 subgroups, each of 5 rats, in 6 test times at 00, 04, 08, 12, 16 and 20 hours. The rats were randomly distributed into groups such that the baseline inter-group differences in body weight, blood pressure and hematocrit of Epo Rx versus saline and other Rx groups were not statistically significant. Blood pressure, hematocrit, and body weight were measured just before and immediately after the completion of a 4-week course of twice-weekly Epo (50 U/kg BW) or physiological saline subcutaneous injections. Epo, Epo-bp, and aEpo-bp dosage was determined based on Epoetin study reports (4). The Epo dose was 50 units per kg body weight, and an Epo-bp and aEpo-bp were administered in an amount equimolar with Epo. The erythropoietin (Epoetin) was from Amgen Company (Thousand Oaks, Calif.). Affinity purified Epo-bp and aEpo-bp were prepared in our laboratories. The antibodies were digested to Fab fragments, and the Fab antibodies were purified.

For blood pressure measurement, the femoral artery was cannulated under pentobarbital (50 mg/kg) anesthesia. At the end of the study, spleens were weighed and photographed. The weights of the brain, heart, aorta, and L- and R-kidneys were also obtained.

Ligand Binding Site in Progenitor Cells and Detection of Epo and EpoR:

We developed ocEpo-bp in sheep innoculated with Epo-bp every 3-4 week for 3 months. After collecting serum, the antibodies were purified and digested to generate Fab antibodies. The Fab were purified. Fab were fluorescein labeled according to the manufacturer's description. These materials were used to detect Epo receptor in blood and/or tissue samples. Negative control cells had no antibodies added and positive control cells had Fab from IgG of preimmune serum. To test for antibody binding sites (Epo receptor) bone marrow cells were washed in PBS and dispensed at 1-3×103 cells per well in round-bottomed tubes and centrifuged into a pellet at 500 g for 2 minutes. Supernatant was removed and 100 [1,1 of fluorescein-conjugated Fab antibodies were added. After mixing well, the mixture was incubated on ice for 30 min. The cells were washed three times by adding 400 mill of buffer containing 1% FCS and 0.01% NaN3 in PBS and centrifuged at 500 g for 2 minutes to remove supernatant. The cells were resuspended in a total volume of up to 50 1.tl of PBS and analyzed under an inverted fluorescence microscope. Enzyme immunoassay (EIA) was used to detect and measure the levels of Epo, Epo-bp, and antibodies against Epo, and Epo-bp in healthy untreated human subjects. EIA microplates were coated with 2 pg/well of anti-Epo to detect Epo and 21.1 g/well of anti-Epo-bp to detect Epo-bp. To detect circulating anti-Epo and anti-Epobp antibodies, wells were coated with 2001.11 of 1:10 diluted serum or plasma in PBS, pH 7.4. Plates were incubated at room temperature for 30 minutes or at 4° C. overnight. After coating the plates with antibody or serum, wells were washed 3 times with 200 .tl/well PBST (0.05% TWEEN 20 in PBS). Nonspecific binding sites were blocked with 200 l/well 1% BSA in PBST for 30 min at room temperature. Wells were washed 3 times with 200 .tl/well PBST. To detect bound antigen, peroxidase-streptavidin label was attached to Fab anti-Epo (for detecting Epo), Epo (for detecting anti-Epo antibodies), Fab anti-Epo-bp (for detecting Epo-bp), and Epobp (for detecting anti-Epo-bp) in our laboratory. Two micrograms of the appropriate 5 peroxidase-streptavidin-labeled protein in 200 ill PBST was added per well. The wells were washed 3 times with 200 piPBST. A solution (160 LID of o-phenylenediaminedihydrochloride (OPD) in citrate buffer was added to each well. (The solution contained 10 mg/ml in 24 mM citrate, 51 mM Na2HPO4, pH 6.0, with 0.4 ml of 3% 1-1202 added to 100 ml of solution immediately before use.) The reaction was stopped by adding 40 [L1 of 5M NaOH, and the absorbance was measured at 405 nm.

Statistics:

Data were analyzed by two-tailed Student's t test, the cosinor method and the linear least square rhythmometry (21), allowing variation as a function of the data. Data are expressed as mean±SEM. A p value of less than 0.05 was considered significant.

Results

In Table 1, before treatment, the inter-group differences for blood pressure, hematocrit, and body weight in all treatment groups were not statistically significant. Overall, body weight was lowered by Epo compared to control (295 vs. 313 grams, $p<0.01$). The reference circadian blood pressure differences in Epo treatment versus control, Epo-bp, and aEpo-bp (Fab antibody against Epo-bp) treatment groups before treatment were not statistically significant (87±2.8 vs. 88.8±3.4, 88.7±2.5, 84.3±2.3 mm Hg). After treatment, the circadian blood pressure was significantly increased in the Epo treated group. The group comparisons between Epo treatment versus control, Epo-bp, and ocEpo-bp treatment groups were as follows: 136.2±2.3 vs. 116.2±1.7, 118.4±2.1 and 116.6±2.1 mm Hg, respectively, each $p<0.0001$. When Epo-bp or aEpo-bp was given along with Epo, however, blood pressure was maintained at similar levels to the saline control group: 118.3±1.7 in the Epo-bp+Epo group and 121.0±2.0 mm Hg in the aEpo-bp+Epo treatment group, which were significantly lower than that of the Epo treat group (136.2±2.3), each $p<0.0001$.

TABLE 1

Overall Effects upon Circadian Body Weight, Blood Pressure, Hematocrit and Other Organ Systems in Various Treatments.

| Group (Rx) (all group n = 30) | BW (g) | ȳ before Rx BP (mm Hg) | Hct (%) |
|---|---|---|---|
| Control (Saline) vs. | 80.1 ± 1.7 | 88.8 ± 3.4 | 36.2 ± 0.7 |
| Epo | 80.2 ± 1.4 | 87.1 ± 2.8 | 37.0 ± 0.6 |

TABLE 1-continued

Overall Effects upon Circadian Body Weight, Blood Pressure, Hematocrit and Other Organ Systems in Various Treatments.

| | | | |
|---|---|---|---|
| Epo-bp | 81.6 ± 1.5 | 88.7 ± 2.5 | 36.5 ± 0.7 |
| αEpo-bp | 81.2 ± 1.3 | 84.3 ± 2.3 | 36.1 ± 0.4 |
| Epo + Epo-bp | 81.0 ± 1.0 | 84.3 ± 3.4 | 36.3 ± 0.6 |
| Epo + αEpo-bp | 79.4 ± 1.5 | 88.9 ± 2.6 | 37.1 ± 0.4 |

| | $\bar{y}$ after Rx | | | | |
|---|---|---|---|---|---|
| | BW (g) | BP (mm Hg) | Hct (%) | SW (g) | Brain W (g) |
| Control (Saline) vs. | 312.8 ± 4.9 | 116.2 ± 1.7 | 42.7 ± 0.8 | 0.86 ± 0.03 | 1.82 ± 0.01 |
| Epo | 294.9 ± 4.2* | 136.2 ± 2.3*** | 61.6 ± 1.3*** | 1.58 ± 0.07*** | 1.77 ± 0.02* |
| Epo-bp | 312.1 ± 3.9 | 118.4 ± 2.1 | 43.9 ± 0.6 | 0.89 ± 0.02 | 1.80 ± 0.02 |
| αEpo-bp | 305.0 ± 4.9 | 116.6 ± 2.1 | 44.1 ± 0.7 | 0.85 ± 0.02 | 1.80 ± 0.01 |
| Epo + Epo-bp | 303.4 ± 3.6 | 118.3 ± 1.7 | 58.0 ± 1.1*** | 1.62 ± 0.05*** | 1.77 ± 0.02* |
| Epo + αEpo-bp | 298.4 ± 4.4 | 121.0 ± 2.0 | 59.1 ± 1.1*** | 1.79 ± 0.07*** | 1.76 ± 0.01** |
| Epo vs. | 294.9 ± 4.2 | 136.2 ± 2.3 | 61.6 ± 1.3 | 1.58 ± 0.07 | 1.77 ± 0.02 |
| Epo-bp | 312.1 ± 3.9* | 118.4 ± 2.1*** | 43.9 ± 0.6*** | 0.89 ± 0.02*** | 1.80 ± 0.02 |
| αEpo-bp | 305.0 ± 4.9 | 116.6 ± 2.1*** | 44.1 ± 0.7*** | 0.85 ± 0.02*** | 1.80 ± 0.01 |
| Epo + Epo-bp | 303.4 ± 3.6 | 118.3 ± 1.7*** | 58.0 ± 1.1‡ | 1.62 ± 0.05 | 1.77 ± 0.02 |
| Epo + αEpo-bp | 298.4 ± 4.4 | 121.0 ± 2.0*** | 59.1 ± 1.1 | 1.79 ± 0.07 | 1.76 ± 0.01 |

| | $\bar{y}$ after Rx | | | |
|---|---|---|---|---|
| | Heart W (g) | Aorta W (g) | R-Kidney W (g) | L-Kidney W (g) |
| Control (Saline) vs. | 1.03 ± 0.02 | 0.046 ± 0.002 | 1.107 ± 0.02 | 1.092 ± 0.02 |
| Epo | 0.93 ± 0.02** | 0.046 ± 0.002 | 1.076 ± 0.02 | 1.084 ± 0.03 |
| Epo-bp | 1.03 ± 0.02 | 0.046 ± 0.002 | 1.106 ± 0.02 | 1.083 ± 0.03 |
| αE-Epo-bp | 1.04 ± 0.02 | 0.044 ± 0.002 | 1.112 ± 0.02 | 1.099 ± 0.02 |
| Epo + Epo-bp | 0.96 ± 0.02* | 0.046 ± 0.002 | 1.098 ± 0.02 | 1.073 ± 0.02 |
| Epo + αEpo-bp | 0.99 ± 0.02 | 0.046 ± 0.002 | 1.084 ± 0.02 | 1.044 ± 0.02 |
| Epo vs. | 0.93 ± 0.02 | | | |
| Epo-bp | 1.03 ± 0.02** | | | |
| αE-Epo-bp | 1.04 ± 0.02** | | | |
| Epo + Epo-bp | 0.96 ± 0.02 | | | |
| Epo + αEpo-bp | 0.99 ± 0.02* | | | |

Rx: treatment; n = number of rats (30 rats in each group); $\bar{y}$: 24-h average; αEpo-bp = anti-Epo-bp antibody;
*$p < 0.01$;
**$p < 0.001$;
***$p < 0.0001$;
‡$p < 0.05$;
g = gram; BW = body weight; BP = blood pressure; Hct = hematocrit; SW = spleen weight; W = weight; R = right; L = left Epo treatment increased hematocrit markedly overall as compared to the saline, Epobp or aEpo-bp groups (61.6 vs. 42.7, 43.9 and 44.1%, respectively) and at each of the 6 test times, all p<0.0001. Administering Epo-bp or aEpo-bp together with Epo had almost no effect on the Epo-induced hematocrit increase (61.6% hematocrit in Epo vs. 58.0% in Epo+Epo-bp and 59.1% in Epo+aEpo-bp Rx). But, significantly, both Epo-bp and aEpo-bp almost eliminated the Epo-induced blood pressure rise (136.2 mm Hg in the Epo-treated group, vs. 116.2 in saline control, 118.3 for Epo+Epo-bp, and 121.0 in Epo+aEpo-bp). Thus, both Epo-bp and aEpo-bp protected the rats from the blood pressure rise caused by Epo treatment.

Splenomegaly characterized each rat in the Epo-treated group (spleen weight overall 1.58 vs. 0.86 for saline, 0.89 for Epo-bp, and 0.85 grams for aEpo-bp, each p<0.0001). Administering Epo-bp or aEpo-bp together with Epo did not affect the splenomegaly. Brain and heart weights were significantly lower in the Epo Rx group as compared to all other groups, although the aorta and kidney weights were similar in each group.

Figure 2:
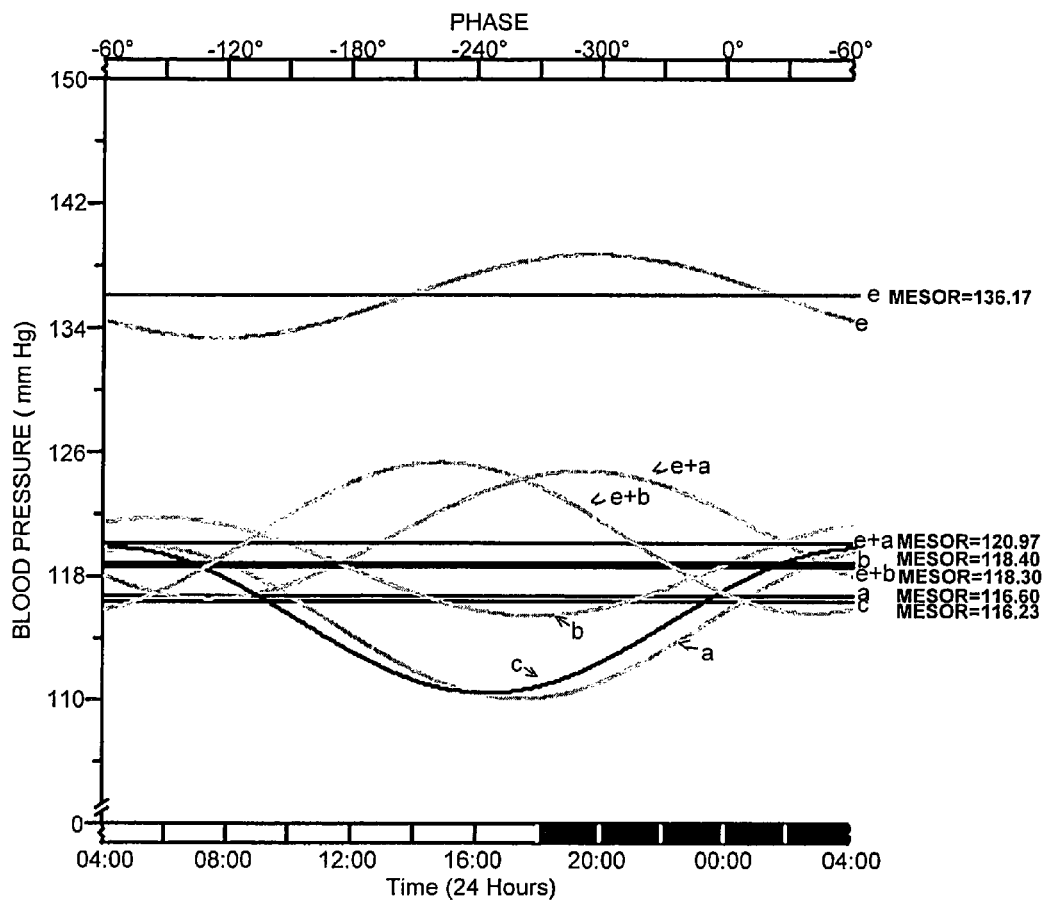
FIG. 2 shows the circadian blood pressure measurements for each of the treatment groups.

FIG. 1 shows circadian blood pressures in all group comparisons in bar graphs±standard errors (SEM). The Epo-treated group had a significantly increased blood pressure as compared to all other 5 groups, each p<0.0001. FIG. 2 shows circadian fluctuations of blood pressure in MESOR (about 24-h mean), amplitude and acrophase (peak time) in each treatment group. Epo treatment increased circadian blood pressure (MESOR) significantly as compared to all other groups (all p<0.0001), although all group amplitude comparisons were not significantly different. After treatment, the peak time in the Epo-treated rats was shifted to the daytime as compared to control, Epo-bp or ocEpo-bp treatment groups (19:40 vs. 04:08, 05:44, 05:16, respectively). It is an obvious shift change from the night to the daytime peak with Epo treatment in this nocturnal animal. When Epo-bp or ocEpo-bp was given together with Epo, the shift change still remained in the same daytime range as in the Epo-alone treatment group (14:48, 19:20, respectively), although the Epo-bp+Epo and aEpo-bp+Epo groups' blood pressure levels were similar to the control group.

Table 2 summarizes the circadian variations of body weight, blood pressure, hematocrit and spleen weight in the 6 subgroups after Epo, Epo-bp and aEpo-bp treatments. The body weight difference between Epo-treated rats and any other treatment group was not statistically significant among the 6 test times. A significantly increased blood pressure in the Epo treated group was detected at 12, 16, 20 and 00 hours, but not at 4.0 or 8.0 hours as compared to control, Epo-bp and aEpo by Rx groups. Epo treatment increased hematocrit markedly overall and at each of the 6 test times as compared to control, Epo-bp and aEpo-bp Rx groups, all p<0.0001. The spleen weights were significantly higher in the Epo-treated group rats than those of the control, Epo-bp and aEpo-bp groups at all time points, although the body weight was lower at each time comparison.

TABLE 2

Circadian Variations of Body Weight, Blood Pressure, Hematocrit and Spleen Weight in Various Treatments

| Group (Rx) | 0400 | 0800 | 1200 | 1600 | 2000 | 0000 |
|---|---|---|---|---|---|---|
| BW (gram): | | | | | | |
| Saline vs. | 313 ± 12 | 305 ± 09 | 324 ± 18 | 308 ± 13 | 310 ± 10 | 317 ± 13 |
| Epo | 305 ± 13 | 294 ± 07 | 294 ± 05 | 290 ± 05 | 295 ± 14 | 291 ± 14 |
| Epo-bp | 314 ± 11 | 310 ± 06 | 303 ± 04 | 312 ± 10 | 319 ± 11 | 319 ± 13 |
| αEpo-bp | 314 ± 10 | 297 ± 20 | 308 ± 13 | 299 ± 06 | 293 ± 05 | 320 ± 12 |
| Epo + Epo-bp | 297 ± 10 | 300 ± 04 | 301 ± 09 | 308 ± 11 | 301 ± 11 | 313 ± 09 |
| Epo + αEpo-bp | 296 ± 13 | 286 ± 06 | 279 ± 04* | 304 ± 12 | 305 ± 05 | 320 ± 13 |
| BP (mmHg): | | | | | | |
| Saline vs. | 116 ± 5.8 | 120 ± 4.6 | 117 ± 3.7 | 108 ± 1.0 | 119 ± 3.2 | 118 ± 4.1 |
| Epo | 131 ± 7.6 | 131 ± 4.8 | 139 ± 3.9* | 128 ± 8.1‡ | 140 ± 6.3* | 137 ± 6.2‡ |
| Epo-bp | 118 ± 4.5 | 122 ± 5.5 | 118 ± 3.6 | 115 ± 4.0 | 118 ± 6.1 | 120 ± 7.7 |
| αEpo-bp | 113 ± 5.7 | 122 ± 5.1 | 117 ± 4.7 | 112 ± 3.4 | 113 ± 4.6 | 122 ± 6.8 |
| Epo + Epo-bp | 114 ± 2.2 | 121 ± 3.1 | 118 ± 6.9 | 121 ± 4.5‡ | 119 ± 4.0 | 117 ± 3.8 |
| Epo + αEpo-bp | 116 ± 6.7 | 121 ± 4.1 | 120 ± 6.2 | 120 ± 5.0‡ | 127 ± 5.6 | 122 ± 1.4 |
| Epo vs. | | | | | | |
| Epo-bp | 118 ± 4.5 | 122 ± 5.5 | 118 ± 3.6* | 115 ± 4.0‡ | 118 ± 6.1‡ | 120 ± 7.7 |
| αEpo-bp | 113 ± 5.7 | 122 ± 5.1 | 117 ± 4.7‡ | 112 ± 3.4‡ | 113 ± 4.6* | 122 ± 6.8 |
| Epo + Epo-bp | 114 ± 2.2 | 121 ± 3.1 | 118 ± 6.9‡ | 121 ± 4.5 | 119 ± 4.0‡ | 117 ± 3.8‡ |
| Epo + αEpo-bp | 116 ± 6.7 | 121 ± 4.1 | 120 ± 6.2‡ | 120 ± 5.0 | 127 ± 5.6 | 122 ± 1.4‡ |
| Hct (%): | | | | | | |
| Saline vs. | 42 ± 2.6 | 41 ± 2.3 | 42 ± 1.6 | 44 ± 0.5 | 45 ± 1.4 | 43 ± 3.0 |
| Epo | 60 ± 4.5* | 64 ± 2.2*** | 66 ± 2.7*** | 65 ± 1.5*** | 61 ± 3.8* | 64 ± 1.5** |
| Epo-bp | 45 ± 1.4 | 45 ± 1.6 | 44 ± 1.1 | 41 ± 2.2 | 45 ± 0.6 | 43 ± 1.9 |
| αEpo-bp | 47 ± 1.0 | 45 ± 0.8 | 43 ± 0.8 | 43 ± 3.2 | 43 ± 2.2 | 44 ± 0.9 |
| Epo + Epo-bp | 58 ± 1.9** | 62 ± 1.8*** | 60 ± 2.9*** | 62 ± 2.5*** | 54 ± 3.2‡ | 53 ± 3.5 |
| Epo + αEpo-bp | 61 ± 2.0*** | 64 ± 1.9*** | 60 ± 2.7*** | 57 ± 4.0‡ | 57 ± 3.2* | 55 ± 1.8* |
| SW (gram): | | | | | | |
| Saline vs. | 0.88 ± 0.1 | 0.82 ± 0.1 | 0.88 ± 0.1 | 0.96 ± 0.1 | 0.73 ± 0.1 | 0.92 ± 0.1 |
| Epo | 1.65 ± 0.2* | 1.70 ± 0.2** | 1.69 ± 0.1*** | 1.63 ± 0.1* | 1.37 ± 0.1* | 1.23 ± 0.1‡ |
| Epo-bp | 0.87 ± 0.0 | 0.87 ± 0.0 | 0.87 ± 0.0 | 0.94 ± 0.1 | 0.97 ± 0.1‡ | 0.83 ± 0.1 |
| αEpo-bp | 0.82 ± 0.0 | 0.92 ± 0.1 | 0.87 ± 0.0 | 0.80 ± 0.1 | 0.79 ± 0.1 | 0.89 ± 0.0 |
| Epo + Epo-bp | 1.50 ± 0.1** | 1.58 ± 0.1*** | 1.67 ± 0.1*** | 1.62 ± 0.2* | 1.48 ± 0.1*** | 1.86 ± 0.1*** |
| Epo + αEpo-bp | 1.69 ± 0.1*** | 1.54 ± 0.2** | 1.53 ± 0.1*** | 1.80 ± 0.1** | 1.90 ± 0.2** | 2.27 ± 0.3** |
| Epo vs. | | | | | | |
| Epo-bp | 0.87 ± 0.0** | 0.87 ± 0.0** | 0.87 ± 0.0*** | 0.94 ± 0.1* | 0.97 ± 0.1 | 0.83 ± 0.1‡ |
| αEpo-bp | 0.82 ± 0.0** | 0.92 ± 0.1* | 0.87 ± 0.0*** | 0.80 ± 0.1** | 0.79 ± 0.1* | 0.89 ± 0.0* |
| Epo + Epo-bp | 1.50 ± 0.1 | 1.58 ± 0.1 | 1.67 ± 0.1 | 1.62 ± 0.2 | 1.48 ± 0.1 | 1.86 ± 0.1* |
| Epo + αEpo-bp | 1.69 ± 0.1 | 1.54 ± 0.2 | 1.53 ± 0.1 | 1.80 ± 0.1 | 1.90 ± 0.2 | 2.27 ± 0.3* |

Rx = Treatment;
n = 5 rats in each subgroup;
*$p < 0.01$;
**$p < 0.001$;
***$p < 0.0001$;
‡$p < 0.05$;
BP = Blood pressure;
BW = Body weight;
Hct = Hematocrit;
SW = Spleen weight.

Figure 3:
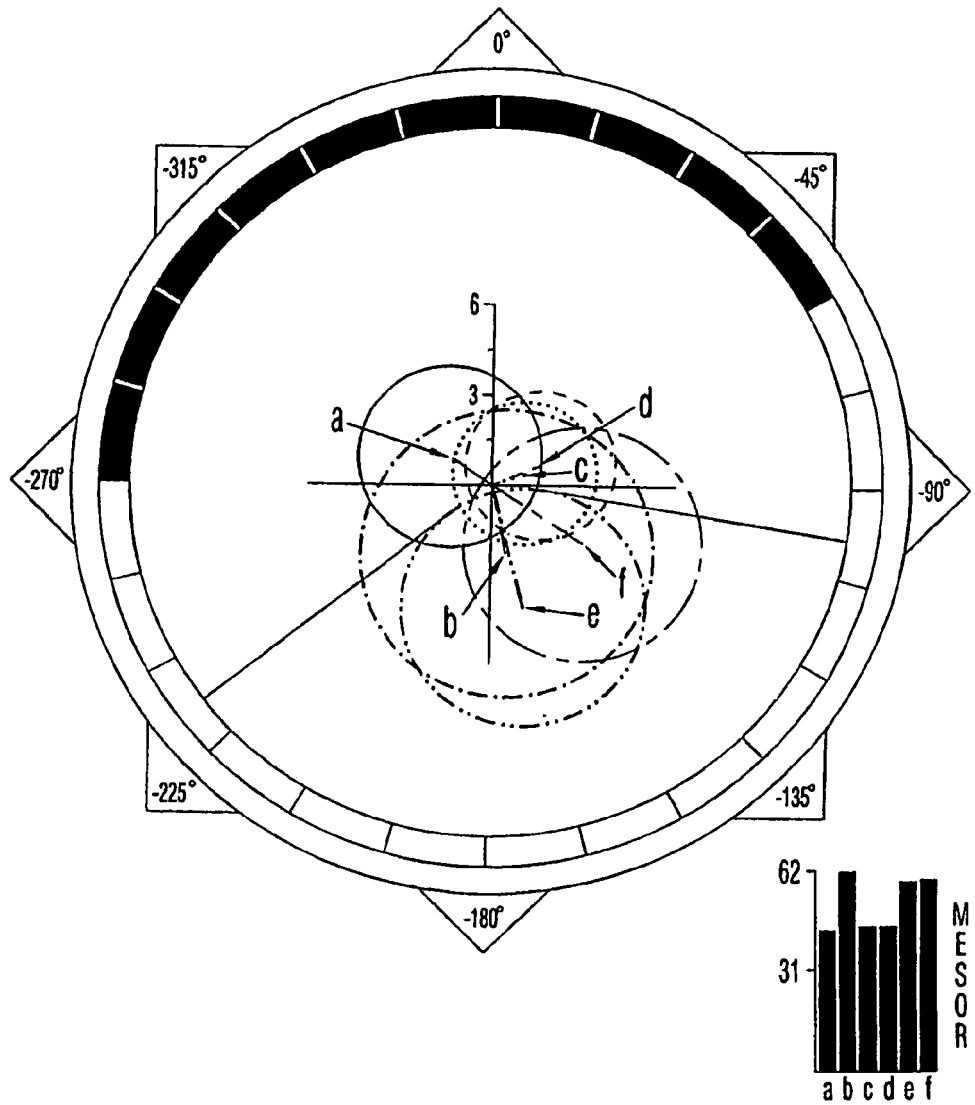
FIG. 3 is a representation of the circadian hematocrit variation in the treatment groups of rats.

FIG. 3 shows circadian hematocrit comparisons. There was not only an increased hematocrit but also the peak time of hematocrit shifted from night (20:15) to a late morning hour (11:16) with Epo-treatment. In the graph, groups of a (control), c (Epo-bp) and d (aEpo-bp) are located in the dark cycle plane, while groups of b (Epo), e (Epo+Epo-bp), and f (Epo±aEpo-bp) are located in the light cycle plane. Again, it is an obvious shift change from the night to the daytime peak in Epo Rx in this nocturnal animal. MESOR comparisons in % hematocrit in Epo (61.6) vs. control (42.7), Epo-bp (43.9) and aEpo-bp (44.1) treatment were all statistically significant in each time point comparison (each $p<0.0001$). The amplitudes of the circadian peak-to-peak differences in hematocrit were not significantly different between the treatment groups. But the amplitudes were larger in the Epo-treated groups than in the groups that did not receive Epo (2.40 in Epo, 4.41 in Epo+Epo-bp, and 3.59 in Epo±aEpo-bp, versus 1.65 in control, 1.13 in Epo-bp and 1.73 in aEpo-bp).

In FIG. 4, splenomegaly (a, b and c) characterized each Epo treated rat when compared with the saline treated rats (FIG. 4, panel d). The spleen weight was significantly higher in Epo treated rats, as compared to those of control, Epo-bp and aEpo-bp Rx groups (Tables 1 and 2). The results suggest that the time of the Epo treatment, with or without Epo-bp and/or aEpo-bp treatment may be important. Epo-bp and aEpo-bp protect against the Epo-caused blood pressure rise, while not reducing the Epo-increased hematocrit levels. Epo dose in clinical use should be reevaluated to prevent further systemic and local adverse effects, such as high blood pressure and other organ damages. The binding sites of blood cell progenitors were identified using Epo-bp and antibodies against it. Fluorescein-labeled aEpo-bp was used to visualize receptor sites of bone marrow progenitor cells. No receptors were detected with fluorescein-labeled preimmune Fab, or in negative control cells. But labeled aEpo-bp did detect binding sites on megakaryocytes, erythroblasts, normoblasts, and myeloblasts (data not shown).

The levels of Epo, Epo-bp, and antibodies against Epo and Epo-bp were measured in serum and plasma in healthy untreated humans by enzyme immunoassay (EIA The EIA results are presented in FIG. 5. Optical density (OD) of each measurement is presented as the mean±SEM of 8-14 individual samples in duplicates. The OD values presented in FIG. 5 were calculated by subtracting the OD value of the blanks from the OD of each sample. Serum and plasma Epo and Epo-bp OD values were similar to each other: 0.308±0.026 serum Epo, 0289±0.022 serum Epo-bp, 0.289±0.028 plasma Epo, and 0.299±0.015 plasma Epo-bp. The plasma level of anti-Epo-bp antibody was significantly lower than those of the other three antibody categories: 0.058±0.008 serum aEpo, 0.052±0.006 serum aEpo-bp, 0.054±0.013 plasma aEpo, and 0.031±0.004 plasma aEpo-bp. Serum aEpo and aEpo-bp levels were similar but the concentration of plasma aEpo-bp was significantly lower than the concentration of serum aEpo, serum aEpo-bp, or plasma aEpo ($p<0.025$). The Epo and Epo-bp values were converted with known Epo concentrations prepared as controls in the same plate to mU/ml. The converted values in mU/ml were 25.4±2.17 mU serum Epo, 24.2±2.35 mU plasma Epo; 24.2±1.84 mU serum Epo-bp, 25.0±1.26 mU plasma Epo-bp. This assay method is simple and more sensitive than the radioimmunoassay (17.7±6.3 mU/ml of Epo) and gives a much smaller SEM. Furthermore, the materials used in the preparation are more environmentally friendly than radioactive or other toxic chemicals used in conventional methods.

Discussion

As expected, we observed an increase in blood pressure in the Epo-treated group. In addition, the hematocrit was markedly increased overall and at each of the 6 test times in the Epo-treated rats, and splenomegaly characterized each rat with the Epo treatment. Epo treatment not only significantly increased blood pressure but also shifted the peak time of blood pressure from the night to the daytime. Remarkably, Epo-bp and aEpo-bp protected the rats almost completely from the Epo-induced rise in blood pressure, while not reducing hematocrit percent. The mechanism of this protective effect is not known. We could speculate, however, that Epoetin (recombinant Epo currently in clinical use) may induce some toxic materials in the living animal body when repetitively injected. Epo-bp and/or ocEpo-bp might bind and eliminate the toxic materials, since Epo-bp binds Epo or its degradation products, and VEpo-bp might also bind certain products induced by Epo treatment.

FIGS. 2 and 3 show that Epo, as well as combination treatment with Epo+Epo-bp or Epo+VEpo-bp caused a shift in the circadian time of peak blood pressure. This suggests that treatment time for treatment with Epo, Epo+Epo-bp, or Epo+VEpo-bp may markedly affect the outcome. An individual's genetic susceptibility to endocrine treatment, as shown by salt susceptibility to hypertension in Dahl rats, also must be considered (22,23).

The cloning of the human Epo-receptor recombinant vector JYL26 and purification of the pure human Epo-bp and its antibodies were important benchmarks to allow us to visualize the ligand binding sites and to identify the cell type where the Epo receptor is located (Lee, U.S. Pat. No. 5,843,726). To identify the ligand binding site, we developed several sensitive and simple methods. These may allow us to understand the structure of the Epo receptor, and examine the factors involved in ligand binding, as well as to identify other factors involved in regulating differentiation and proliferation of the progenitor cells. In this study, we report the direct binding of Epo to our purified human Epo-bp. Our Epo-bp and its antibodies are to our knowledge the first purified pure human Epo receptor gene products, which are characterized in specific binding of Epo and its antibodies in nM concentrations. The binding sites of blood progenitor cells were elaborated using Epo-bp and its antibodies. These data support the current proposal that all human progenitor blood cells contain Epo receptors and bind Epo. We do not know what the biophysiological mechanisms of Epo or the second messenger system involved in response to the Epo-Epo receptor interaction are. The methods presented in this report will help identify defects related to Epo or Epo receptor, and elucidate the role of Epo receptor (EpoR) in progenitor processes and ligand binding. The results may help in understanding the structural and functional relationship of Epo-EpoR interactions in blood cell progenitors. The sensitive detection may help us to understand the role of the Epo-EpoR interaction in blood cell production and diseases of blood cell production and help to develop treatment methods for hematological malignancies and some systemic cardiovascular diseases, such as high blood pressure.

Conclusions

Epo treatment increased hematocrit markedly overall as compared to the saline control, Epo-bp, and anti-Epo-bp antibody (aEpo-bp) treated groups, and did so at each of the 6 test times, all $p<0.0001$. Increased blood pressure was detected at 12, 16, 20 and 00 hours, but not at 04 or 08 hours in rats treated with Epo. When Epo-bp or aEpo-bp was given in conjunction with Epo treatment, blood pressure was maintained at similar levels to the control group. However, hematocrit levels were not significantly changed in Epo treatment vs. Epo+Epo-bp or Epo+aEpo-bp treatment groups (61.6 vs. 58.0 or 59.1%, respectively). Thus, Epo-bp and aEpo-bp reduce or prevent the Epo-induced rise in blood pressure.

Body weight was lowered by Epo treatment. Splenomegaly characterized each rat in Epo treatment. Brain and heart weights were significantly lower in the Epo treated group as compared to all other groups. These data suggest that Epo dose should be reevaluated to prevent further organ damage. The circadian results indicate that the time of the Epo treatment, alone or in combination of Epo-bp and/or aEpobp, may also be important.

Serum and plasma levels of Epo, Epo-bp, and antibodies against the proteins in untreated human volunteers were determined. Serum and plasma Epo and Epo-bp levels were similar: Epo 25.4±2.17; 24.2±2.35; and Epo-bp 24.2±1.84; 25.0±1.26 mU/ml, respectively. Serum aEpo and aEpo-bp levels were similar, but the plasma aEpo-bp level was significantly lower than that of serum or plasma aEpo or serum aEpo-bp.

REFERENCES CITED

1. Ifudu 0, Dawood M, Homel P: Erythropoietin-induced elevation in blood pressure is immediate and dose dependent. *Nephron* 1998; 79(4):486-487.
2. Schiffl H, Lang S M: Hypertension induced by recombinant human erythropoietin (rHU-Epo) can be prevented by indomethacin. Pathogenetic role of cytosolic calcium. *European J Med Res* 1997; 2(3):97-100.
3. Gobel B O, Schulte-Gebel A, Weisser B, Glanzer K, Vetter H, Dusing R: Arterial blood pressure: Correlation with erythrocyte count, hematocrit, and hemoglobin concentration. *Am. J. Hypertens* 1991; 4(1): 14-19.
4. Faulds D, Sorkin E M: Epoetin (Recombinant Human Erythropoietin). A review of its pharmacodynamic and pharmacokinetic properties and therapeutic potential in anemia and the stimulation of erythropoiesis. *Drugs* 1989; 38(6):863-899.
5. Raine A E G: Hypertension, blood viscosity, and cardiovascular morbidity in renal failure: implications of erythropoietin therapy. *Lancet* 1988; 1:97-100.
6. Buckner F S, Eschbach J W, Haley N R, Davidson R C, Adamson J W: Hypertension following erythropoietin therapy in anemic hemodialysis patients. *Am J Hypertens* 1990; 3:947-955.
7. Kong D H, Yoon K I, Han D S: Acute effects of recombinant human erythropoietin on plasma levels of proendothelin-1 and endothelin-1 in haemodialysis patients. Nephrol, Dialysis, *Transplantation* 1998; 13(11): 2877-2883.
8. Lebel M, Lacasse M S, Lariviere R, Kingma I, Grose J H: Plasma and blood vessel endothelin-1 concentration in hypertensive uremic rats treated with erythropoietin. *Clin & Exp Hypertens* 1998; 20(8):939-951.
9. Vogal V, Kramer H J, Backer A, Meyer-Lehnert H, Jelkmann W, Frandrey J: Effects of erythropoietin on endothelin-1 synthesis and the cellular calcium messenger system in vascular endothelial cells. *Am J Hypertens* 1997; 10(3):289-296.
10. Carlini R G, Dusso A S, Obialo C L, Alvarez U M, Rothstein M: Recombinant human erythropoietin increases endothelin-1 release by endothelial cells. *Kidney Int* 1993; 43:1010-1014.
11. Schmieder R E, Langenfeld M R, Hilgers K F: Endogenous erythropoietin correlates with blood pressure in essential hypertension. *Am J Kidney Dis* 1997; 29(3):376-382.
12. Canadian erythropoietin study group: Effect of recombinant human erythropoietin therapy on blood pressure in hemodialysis patients. *Am J Nephrol* 1991; 11:23-26.
13. Nowicki M: Erythropoietin and hypertension. *J Hum Hypertens* 1995; 9:81-88.
14. Abraham P A, Macres M G: Blood pressure in hemodialysis patients during amelioration of anemia with erythropoietin. *J Am Soc Nephrol* 1991; 2:927-936.
15. Barrett J D, Zhang Z, Zhu J H, Lee D B N, Ward H J, Jamgotchian N, Hu M S, Fredal A, Giordani M, Eggena P: Erythropoietin upregulates angiotensin receptors in cultured rat vascular smooth muscle cells. *J Hypertens* 1998; 16:1749-1757.
16. Fisher J W: Erythropoietin: Physiologic and Pharmacologic aspects. *Proc Soc Exp biol Med* 1997; 216:358-369.
17. Mayeux P, Billat C, Jacquot R: The erythropoietin receptor of rat erythroid progenitor cells. Characterization and affinity cross-linkage. *J Biol Chem* 1987; 262:13985-13990.
18. Wang F F, Kung C K-H, Goldwater E: Some chemical properties of human erythropoietin. *Endocrinology* 1985; 116; 2286-2292.
19. Egrie J C, Strickland T W, Lane J, Aoki K, Cohen A M, Smalling R. Trail G. Lin F K. Browne J K. Hines D K: Characterization and biological effects of recombinant human erythropoietin. *Immunology* 1986; 172:213-224.
20. Lin F K, Lin C H, Lai P H, Browne J K, Egrie J C, Smalling R, Fox G M, Chen K K, Castro M, Suggs S: Monkey erythropoietin gene: cloning, expression and comparison with the human erythropoietin gene. *Gene* 1986; 44(2-3):201-209.
21. Mojon A, Fernandes J R, Hermida R C: Chronolab: An Interactive software package for chronobiologic time series analysis written for the Macintosh computer. *Chronobiol Intern* 1992; 9(6):403-412.
22. Dahl L, Heine M, Tassimiani M: Role of genetic factors in susceptibility to essential hypertension due to chronic excess salt ingestion. *Nature* 1962; 194:480-482.
23. Lee J Y, Tobian L, Hanlon S, Hamer R, Johnson M A, Iwai J: How is the NaCl signal transmitted in NaCl-induced hypertension? *Hypertension* 1989; 13:668-675.

All of the patents, patent documents, and references cited herein are hereby incorporated by reference thereto.

The invention claimed is:

1. An improved method of treatment for anemia involving the administration of erythropoietin comprising:
    administering into a patient's cardiovascular circulatory system erythropoietin along with separately and contemporaneously administering into the patient cardiovascular circulatory system an erythropoietin binding protein comprising (a) or (b),
        wherein (a) is a protein consisting of an amino acid sequence of at least 30 consecutive residues of SEQ ID NO: 2, and (b) is a protein consisting of an amino acid sequence that is at least 90% identical to SEQ ID NO: 2; wherein the erythropoietin is administered in a dosage of 75% to 125% of the molar dosage of the erythropoietin administered to the patient; and wherein the erythropoietin binding protein administered to the patient reduces or eliminates the life-threatening side effect of hypertension occurring in patients that is associated with traditional erythropoietin based anemia treatment.

2. The improved method of treatment of claim 1, wherein the administration of the erythropoietin and erythropoietin-binding protein occurs twice weekly.

* * * * *